US00PP22864P2

(12) United States Plant Patent

Klemm et al.

(10) Patent No.: US PP22,864 P2

(45) Date of Patent: Jul. 17, 2012

(54) *CALIBRACHOA* PLANT NAMED 'KLECA10219'

(50) Latin Name: ***Calibrachoa* sp.**
Varietal Denomination: KLECA10219

(75) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 13/065,566

(22) Filed: Mar. 24, 2011

(51) Int. Cl.
*A01H 5/00* (2006.01)

(52) U.S. Cl. ..... Plt./413

(58) Field of Classification Search ..... Plt./413
See application file for complete search history.

*Primary Examiner* — Annette Para

(74) *Attorney, Agent, or Firm* — Jondle & Associates, P.C.

(57) ABSTRACT

A new *Calibrachoa* plant named 'KLECA10219' particularly distinguished by early flowering and yellow-colored flowers with red centers, is disclosed.

1 Drawing Sheet

Genus and species: *Calibrachoa* sp.
Variety denomination: 'KLECA10219'.

BACKGROUND OF THE NEW PLANT

The present invention comprises a new and distinct variety of *Calibrachoa*, botanically known as *Calibrachoa* sp. and hereinafter referred to by the variety name 'KLECA10219'. The new variety was the result of a controlled cross conducted in June 2007 in Stuttgart, Germany, between the female parent, proprietary *Calibrachoa* plant 'KLECA08187' (U.S. Plant Pat. No. 21,020), and the male parent, proprietary *Calibrachoa* plant 'MF Peach'. A single plant selection was subsequently chosen for further evaluation and asexual propagation.

The new variety was first propagated in May 2008 in Stuttgart, Germany and has been asexually reproduced repeatedly by vegetative cuttings and in-vitro propagation over more than forty-five generations. The present invention has been found to retain its distinctive characteristics through successive asexual propagations via vegetative cuttings.

No Plant Breeder's Rights for this variety have been applied for. 'KLECA10219' has not been made publicly available or sold more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. Early flowering; and
2. Yellow-colored flowers with red centers.

DESCRIPTION OF THE PHOTOGRAPH

This new *Calibrachoa* plant is illustrated by the accompanying photograph which shows inflorescences and foliage of the plant. The colors shown are as true as can be reasonably obtained by conventional photographic procedures. The photograph was taken in May 2010 of a 5-month old *Calibrachoa* plant grown in a 10 centimeter pot in a glass greenhouse in Stuttgart, Germany under normal horticultural practices.

DESCRIPTION OF THE NEW VARIETY

The following detailed descriptions set forth the distinctive characteristics of 'KLECA10219'. The data which defines these characteristics were collected from asexual reproductions carried out in Stuttgart, Germany. The plant history was taken in May 2010 of 5-month old plants grown in 10 centimeter pots in a glass greenhouse with a minimum pinch date of one week. Color readings were taken under natural light. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family*.—Solanaceae.
- *Botanical*.—*Calibrachoa* sp.
- *Common*.—*Calibrachoa* Hybrid.

Parentage:
- *Female*.—The proprietary *Calibrachoa* plant 'KLECA08187', (U.S. Plant Pat. No. 21,020).
- *Male*.—The proprietary *Calibrachoa* plant 'MF Peach'.

Growth:
- *Form*.—Mounding.
- *Habit*.—Semi-trailing.
- *Height* (*measured from the top of the soil*).—12.0 cm.
- *Width* (*horizontal plant diameter*).—17.0 cm.
- *Time to produce a finished flowering plant*.—8 weeks after potting.
- *Outdoor plant performance*.—Continuously flowering, good.
- *Time to initiate and develop roots*.—18 days.
- *Root description*.—Moderate density, freely branching.
- *Root color*.—RHS 155D.

Stems:
- *Length of basal branches*.—9.0 cm.
- *Internode length*.—1.5 cm to 3.0 cm.

*Diameter of branches* (*from midpoint*).—7.0 cm to 9.0 cm.
*Stem color*.—RHS 146B.
*Texture* (*both surfaces*).—Smooth.
*Anthocyanin*.—Absent.
*Pedicel*.—Color: RHS 146C. Length: 1.8 cm. Diameter: 0.1 cm. Texture (both surfaces): Smooth.

Leaves:
*Arrangement*.—Alternate.
*Size*.—Length: 1.5 cm to 2.5 cm. Width: 0.5 cm to 1.0 cm.
*Shape*.—Lanceolate to elliptic.
*Apex*.—Broad acute.
*Base*.—Attenuate.
*Margin*.—Entire.
*Color* (*both immature and mature leaves*).—Upper surface: RHS 139A. Lower surface: RHS 138A.
*Texture* (*both surfaces*).—Smooth.
*Venation pattern*.—Pinnate.
*Venation color*.—RHS 145A.
*Petioles*.—Absent.

Flower bud:
*Shape*.—Irregular to oblong.
*Size*.—Length: 1.8 cm. Diameter: 0.6 cm.
*Color at tight bud*.—RHS 1D.

Inflorescence:
*Blooming habit*.—Continuous flowering during summertime.
*Inflorescence type*.—Single flower, determinate inflorescence.
*Floret type*.—Funnel-shaped, single flowers.
*Lastingness of individual blooms on the plant*.—5 days.
*Fragrance*.—Absent.

Flowers:
*Immature flower*.—Diameter: Horizontal: 1.7 cm. Vertical: 1.8 cm. Color: Upper surface: RHS 7A and RHS 42A. Lower surface: RHS 7B and RHS 42B.
*Mature flower*.—Diameter: Horizontal: 2.2 cm. Vertical: 2.1 cm. Color: Upper surface: RHS 7A and RHS 42B. Lower surface: RHS 7B and RHS 42B.
*Corolla tube*.—Color inside: RHS 6B. Color outside: RHS 7A and RHS 42B. Tube length: 1.2 cm. Texture (outside): Moderate.
*Petals*.—Apex: Obverse. Base: Open and fused into the tube. Margin: Entire. Waviness of petals: Weak. Lobation: Weak. Texture (both surfaces): Smooth.
*Sepals*.—Calyx (composition): Rosette, actinomorphic. Shape: Lanceolate to elliptic. Apex: Acute. Base: Open and tube is fused into the base. Margin: Entire. Length: 1.0 cm. Width: 0.2 cm. Color: Upper surface: RHS 146A. Lower surface: RHS 147B. Texture (both surfaces): Smooth.

Reproductive organs:
*Stamens*.—Number: 5. Filament color: RHS 154A. Filament length: 0.8 cm. Filament diameter: 0.1 cm. Pollen color: RHS 11A. Pollen quantity: Sparse.
*Pistils*.—Number: 1. Length: 0.5 cm. Diameter: 0.2 cm. Stigma color: RHS 149A. Style color: RHS 149A.

Fruit and seed set: No fruit or seed set observed.

COMPARISON WITH PARENTAL AND COMMERCIAL VARIETIES

'KLECA10219' differs from the female parent *Calibrachoa* plant 'KLECA08187', (U.S. Plant Pat. No. 21,020) in that 'KLECA10219' has yellow-colored flowers with red centers, and a less vigorous growth habit, whereas 'KLECA08187' has yellow-orange colored flowers with red centers, and a more vigorous growth habit.

'KLECA10219' differs from the male parent *Calibrachoa* plant 'MF Peach' in that 'KLECA10219' has yellow-colored flowers with red centers, whereas 'MF Peach' has orange-red colored flowers with red centers.

'KLECA10219' differs from the commercial cultivar 'KLECA06120' (U.S. Plant Pat. No. 19,488), in that 'KLECA10219' has a semi-trailing and mounding growth habit, whereas 'KLECA06120' has an upright growth habit.

We claim:

1. A new and distinct variety of *Calibrachoa* plant named 'KLECA10219' as shown and described herein.

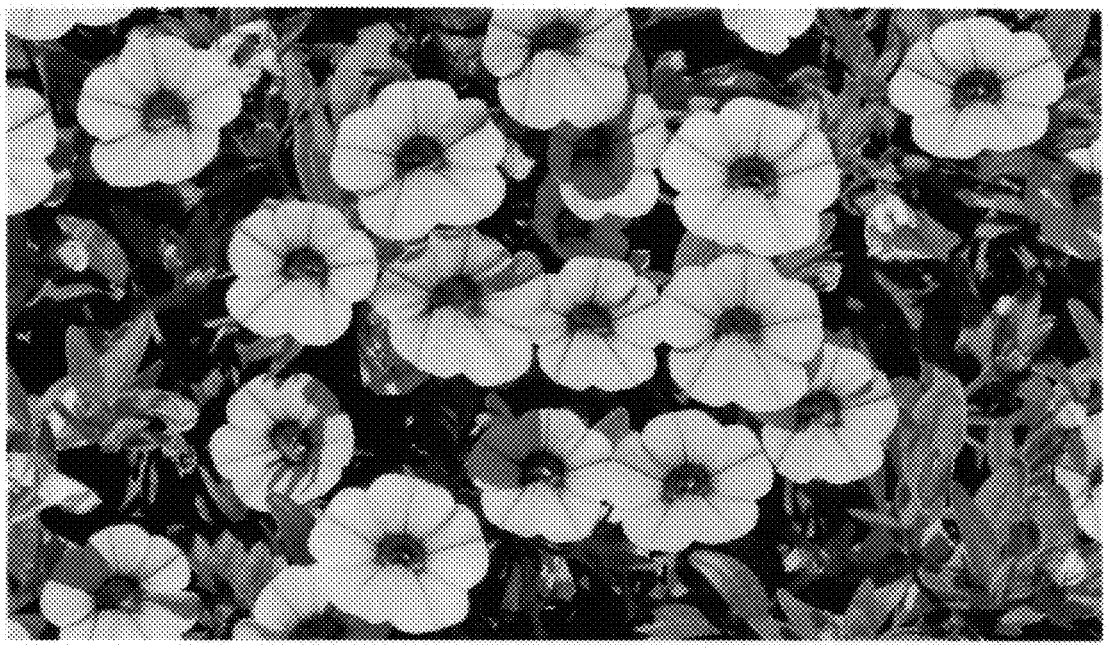

* * * * *